United States Patent
Bjork et al.

(10) Patent No.: US 10,995,356 B2
(45) Date of Patent: *May 4, 2021

(54) CULTURE DEVICE FOR LACTIC ACID BACTERIA

(71) Applicant: 3M INNOVATIVE PROPERTIES COMPANY, St. Paul, MN (US)

(72) Inventors: Jason W. Bjork, Cottage Grove, MN (US); Evan D. Brutinel, Inver Grove Heights, MN (US); Adam J. Stanenas, Cottage Grove, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 61 days.

This patent is subject to a terminal disclaimer.

(21) Appl. No.: 15/569,579

(22) PCT Filed: Apr. 26, 2016

(86) PCT No.: PCT/US2016/029303
§ 371 (c)(1),
(2) Date: Oct. 26, 2017

(87) PCT Pub. No.: WO2016/176173
PCT Pub. Date: Nov. 3, 2016

(65) Prior Publication Data
US 2018/0312895 A1    Nov. 1, 2018

Related U.S. Application Data

(60) Provisional application No. 62/154,312, filed on Apr. 29, 2015.

(51) Int. Cl.
*C12Q 1/04* (2006.01)
*C12M 1/22* (2006.01)
(Continued)

(52) U.S. Cl.
CPC .............. *C12Q 1/04* (2013.01); *C12M 23/04* (2013.01); *C12M 23/20* (2013.01); *C12M 25/06* (2013.01);
(Continued)

(58) Field of Classification Search
CPC .............................. C12Q 1/04; C12M 41/34
See application file for complete search history.

(56) References Cited

U.S. PATENT DOCUMENTS 3,338,794 A    8/1967   Bladel
4,565,783 A    1/1986   Hansen et al.
(Continued)

FOREIGN PATENT DOCUMENTS

GB    2 083 496      3/1982
GB    2 083 496 A    3/1982
(Continued)

OTHER PUBLICATIONS

Synbiosis ("Protocol 3: User Manual" SynBiosis, A division of Synoptics, Cambridge, UK, Frederick MD, 2011-2012, available at 800ezmicro.com/equipment/colony-counters/43-protocol-3.html)(Year: 2012).*

(Continued)

*Primary Examiner* — Robert J Yamasaki
*Assistant Examiner* — Charles Zoltan Constantine
(74) *Attorney, Agent, or Firm* — Eric E. Silverman (57) ABSTRACT

The present disclosure provides a culture device for enumerating colonies of microorganisms. The device can comprise a base, a coversheet, and a nonporous spacer member disposed therebetween. The spacer member comprises an aperture that defines a growth compartment. Disposed in the growth compartment are a cold water-soluble gelling agent, a dry oxygen-scavenging reagent, a dry buffer system, and an effective amount of a dry carbon dioxide-generating (Continued)

reagent. The buffer system is selected such that, when the growth compartment is hydrated with a predetermined volume of deionized water, an aqueous mixture with a pH less than or equal to 6.35 is formed.

20 Claims, 2 Drawing Sheets

(51) Int. Cl.
*C12M 1/14* (2006.01)
*C12M 1/12* (2006.01)
*C12M 1/34* (2006.01)
*C12M 1/00* (2006.01)
*C12N 1/20* (2006.01)
*C12P 7/56* (2006.01)

(52) U.S. Cl.
CPC ............ *C12M 41/34* (2013.01); *C12M 41/36* (2013.01); *C12N 1/20* (2013.01); *C12P 7/56* (2013.01)

(56) References Cited

U.S. PATENT DOCUMENTS

| | | | |
|---|---|---|---|
| 4,605,617 A | 8/1986 | Kasugai | |
| 4,775,626 A * | 10/1988 | Armenta | C12M 23/08 435/189 |
| 5,089,413 A | 2/1992 | Nelson et al. | |
| 5,232,838 A | 8/1993 | Nelson et al. | |
| 5,681,712 A | 10/1997 | Nelson | |
| 6,689,438 B2 | 2/2004 | Kennedy et al. | |
| 2004/0101954 A1 | 5/2004 | Graessle et al. | |
| 2004/0102903 A1 | 5/2004 | Graessle et al. | |
| 2005/0239200 A1 * | 10/2005 | Beckwith | C12M 23/04 435/299.1 |
| 2012/0094327 A1 * | 4/2012 | Young | C12Q 1/04 435/39 |

FOREIGN PATENT DOCUMENTS

| | | |
|---|---|---|
| JP | 55-081593 | 6/1980 |
| JP | 57-039776 | 3/1982 |
| JP | 58-056679 | 4/1983 |
| JP | 11-506910 | 6/1999 |
| WO | WO 1996/38533 | 12/1996 |
| WO | WO 2005/024047 | 3/2005 |
| WO | WO 2005/108545 | 11/2005 |
| WO | WO 2010/147918 | 12/2010 |
| WO | WO 2015/061213 | 4/2015 |

OTHER PUBLICATIONS

Microbiology International ("Protocol 3: Colony counting and zone measuring Automated Imaging", available at 800ezmicro.com/equipment/colony-counters/43-protocol-3.html) (Year: 2012).*

Frey ("Blood, Sweat, and Buffers: pH Regulation During Exercise", 2007, Washington University in St. Louis, General Chemistry Lab Tutorials, available at www.chemistry.wustl.edu/~edudev/LabTutorials/CourseTutorials/bb/Buffer/Buffer.htm). (Year: 2007).*

* cited by examiner

CULTURE DEVICE FOR LACTIC ACID BACTERIA

CROSS REFERENCE TO RELATED APPLICATIONS

This application is a national stage filing under 35 U.S.C. 371 of PCT/US2016/029303, filed Apr. 26, 2016, which claims the benefit of U.S. Provisional Patent Application No. 62/154,312, filed Apr. 29, 2015, the disclosure of which is incorporated by reference in its entirety herein.

BACKGROUND

Many bacteria are sensitive to oxygen and will not grow in its presence. It can be useful in various environments to determine the viability of such anaerobic microorganisms. For example, it can be important to determine if anaerobic microorganisms are present in food and beverage processing and/or packaging facilities. It can also be important to determine the presence of anaerobic microorganisms in medical environments, for example, to determine the presence of pathogens in diagnostic assays. As another example, water treatment facilities test water samples to determine the presence or absence of such microbes.

A variety of devices are available for culturing microorganisms. For example, microorganisms have long been cultured using Petri dishes. As known in the art, Petri dishes are round, shallow, flat bottomed dishes with a suitable medium for growth of the microorganism, such as agar and nutrients. The use of agar medium, however, can be inconvenient and time consuming. For example, agar medium must be sterilized, melted and cooled prior to addition of the sample.

In addition, it can be difficult to provide an environment suitable for culturing anaerobic microorganisms, such as anaerobic lactic acid-producing bacteria using Petri dishes. Because anaerobic microorganisms do not thrive in the presence of oxygen, cumbersome physical and chemical techniques can be required to grow such organisms. Typically, such devices must be modified, i.e., shaped or configured, to provide a physical barrier to the transmission of oxygen.

Other techniques have been developed that use chemical agents incorporated into an anaerobic culturing device to remove oxygen. Generally, such devices include a reducing agent or sterile membrane fragments of bacteria incorporated into a gel or nutrient media. In addition, U.S. Pat. No. 3,338,794 describes an anaerobic bacteria culturing device formed of oxygen impermeable film layers and a nutrient media between the films, which includes a reducing compound.

These and other devices, however, can also be cost prohibitive and may not be readily disposable. These devices can also be cumbersome to assemble and/or use. Although attempts have been made to produce a simple device for culturing anaerobic microorganisms in an aerobic environment, there remains a need for improved anaerobic culture devices.

SUMMARY

In general, the present disclosure relates to detection and, optionally, enumeration of microorganisms in a sample. In particular, the present disclosure relates to growth and detection of microaerotolerant, microaerophilic, or obligately-anaerobic microorganisms. It is now known this growth and detection can be conducted using a self-contained anaerobic environment-generating culture device.

The inventive culture device and methods disclosed herein provide for growth, detection, and differentiation of microaerotolerant and obligately-anaerobic lactic acid bacteria (LAB) even while incubating the microorganisms in oxygen-containing (e.g., normal atmospheric oxygen-containing) environments. Advantageously, this eliminates the need for specialized incubation equipment and reagents (e.g., anaerobe jars, single-use anaerobe sachets, palladium catalysts, anaerobic glove boxes) that are typically required to culture anaerobic microorganisms. Additionally, the inventive methods provide for differentiation of bacteria by permitting detection of the production of carbon dioxide gas from individual colonies, thus eliminating the additional incubation time needed for isolation of pure cultures and the use of fermentation tubes to detect gas production. Furthermore, the disclosure relates to the enumeration of microaerotolerant, or obligately-anaerobic lactic acid bacteria in a sample. Microaerotolerant and obligately-anaerobic microorganisms share the common feature that they require reduced-oxygen environments in which to grow and reproduce.

A further benefit of a device of the present disclosure is the buffering capacity. This eliminates the need to pH-adjust food samples and/or it keeps the culture medium in the device at an optimal pH for a longer period of time.

In one aspect, the present disclosure provides a culture device for enumerating colonies of microorganisms. The device can comprise a base having opposing inner and outer surfaces, a coversheet having opposing inner and outer surfaces, and a nonporous spacer member disposed between the base and the cover sheet. The spacer member comprises an aperture that defines a shape and a depth of a growth compartment. The spacer member and the growth compartment are disposed between the inner surface of the base and the inner surface of the coversheet. The device further can comprise a first effective amount of a dry oxygen-scavenging reagent; a dry buffer system disposed in the growth compartment that, when the growth compartment is hydrated with a predetermined volume of deionized water, forms an aqueous mixture with a pH less than or equal to 6.35; and a second effective amount of a dry carbon dioxide-generating reagent; disposed in the growth compartment. The gelling agent is adhered to the base or the coversheet in the growth compartment.

In any of the above embodiments, the oxygen-scavenging reagent can consist essentially of particles having a diameter of less than 106 microns. In any of the above embodiments, the carbon dioxide-generating reagent can consist essentially of particles having a diameter of less than 106 microns. In any of the above embodiments, the culture device further may comprise a nutrient, an indicator reagent, a selective agent, or a reducing agent disposed in the growth compartment. In any of the above embodiments, the nutrient, the indicator reagent, the selective agent, or the reducing agent, if present in the growth compartment, can be adhered to the base or the coversheet. In any of the above embodiments, the oxygen-scavenging reagent can be selected from the group consisting of ferrous iron or a salt thereof or ascorbic acid or a salt thereof. In any of the above embodiments, the carbon dioxide-generating reagent can be selected from the group consisting of sodium bicarbonate and sodium carbonate.

In another aspect, the present disclosure provides a method of detecting lactic acid bacteria in a sample. The method can comprise opening the culture device of any one of the preceding embodiments to provide access to the growth compartment therein, placing a predefined volume of aqueous liquid into the growth compartment, placing a sample into the growth compartment, closing the culture device, incubating the culture device for a period of time sufficient to permit formation of a microbial colony in the culture medium, and detecting the microbial colony. Placing the aqueous liquid and the sample into the growth compartment and closing the culture device can comprises forming a semi-solid microbial culture medium enclosed by the base, the coversheet, and the spacer of the culture device. The culture medium can have a pH between 4.0 and 6.35.

In any of the above embodiments, incubating the culture device for a period of time comprises incubating the culture device for the period of time in an aerobic atmosphere. In any of the above embodiments of the method, detecting a microbial colony further comprises enumerating one or more optically-detectable colonies in the culture device. In any of the above embodiments of the method, enumerating one or more microbial colonies further comprises distinguishing carbon dioxide-producing colonies from non-carbon dioxide-producing colonies.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a nutrient can be interpreted to mean "one or more" nutrients.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to detection and, optionally, enumeration of microorganisms in a sample. For example, the present disclosure relates to growth and detection of a diverse group of microorganisms collectively known as Lactic Acid Bacteria (hereinafter, "LAB"). LAB are characterized by ability to ferment glucose primarily to lactic acid ("homofermentative" lactic acid bacteria) or to lactic acid, carbon dioxide, and ethanol ("heterofermentative" lactic acid bacteria). It is now known this growth and detection of LAB microorganisms can be conducted using a self-contained anaerobic environment-generating and enriched carbon dioxide environment-generating culture device.

Certain microorganisms grow anaerobically. In addition, other microorganisms such as LAB are capable of growing in the presence of oxygen (i.e., they are "aerotolerant"). Although their fermentative metabolism is used to produce certain foods (e.g., yogurt, cheese, sauerkraut), they are also known as agents of food spoilage in processed meats, beer, and wine, for example.

It is now known that a dry, rehydratable self-contained anaerobic environment-generating and enriched carbon dioxide environment-generating culture device can be made. The culture device comprises an effective amount of a substantially-dry oxygen-scavenging reagent disposed in a growth zone of the culture device and being capable of rehydration in a predetermined volume of aqueous solution wherein, upon rehydration, the oxygen-consuming reagent is capable of participating in an oxygen-consuming reaction. Further, it is now known the oxygen-consuming reaction can consume enough oxygen to facilitate growth of an anaerobic lactic acid bacteria microorganism. Furthermore, the culture device can be held in an aerobic environment wherein the culture device can maintain a reduced oxygen environment for at least about eight days in order to facilitate growth of the aforementioned microorganisms.

The dry, rehydratable culture devices disclosed herein provide a number of advantages over the art. For example, most techniques for enumerating and identifying anaerobic microorganisms involve the use of liquid culture medium (e.g., broth or agar) that is autoclaved before use. The high temperature of sterilization tends to drive most oxygen out of the liquid media. After sterilization, agitation and/or exposure to air can reintroduce oxygen into the medium. In contrast, a device of the present disclosure contains ingredients that generate the desired anaerobic environment for culturing anaerobic or microaerophilic microorganisms.

Bacterial species of interest can be analyzed in a test sample that may be derived from any source, such as a physiological fluid, e.g., blood, saliva, ocular lens fluid, synovial fluid, cerebral spinal fluid, pus, sweat, exudate, urine, mucus, mucosal tissue (e.g., buccal, gingival, nasal, ocular, tracheal, bronchial, gastrointestinal, rectal, urethral, ureteral, vaginal, cervical, and uterine mucosal membranes), lactation milk, feces or the like. Further, the test sample may be derived from a body site, e.g., wound, skin, anterior nares, nasopharyngeal cavity, nasal cavities, anterior nasal vestibule, scalp, nails, outer ear, middle ear, mouth, rectum, vagina, axilla, perineum, anus, or other similar site.

Besides physiological fluids, other test samples may include other liquids as well as solid(s) dissolved or suspended in a liquid medium. Samples of interest may include process streams, water, food, food ingredients, beverages, soil, plants or other vegetation, air, surfaces (e.g., walls, floors, equipment, utensils in a manufacturing plant, hospital, clinic, or home, for example), and the like.

Non-limiting examples of genera of Lactic Acid Bacteria that can be detected and enumerated in the devices and methods of the present disclosure include genera that belong to the order Lactobacillales. These genera include, for example, *Lactobacillus, Leuconostoc, Pediococcus, Lactococcus,* and *Streptococcus*. Other genera of LAB that can be detected and enumerated in the devices and methods of the present disclosure include, for example, *Carnobacterium, Enterococcus, Oenococcus, Tetragenococcus, Vagococcus,* and *Weisella*.

Figure 1:
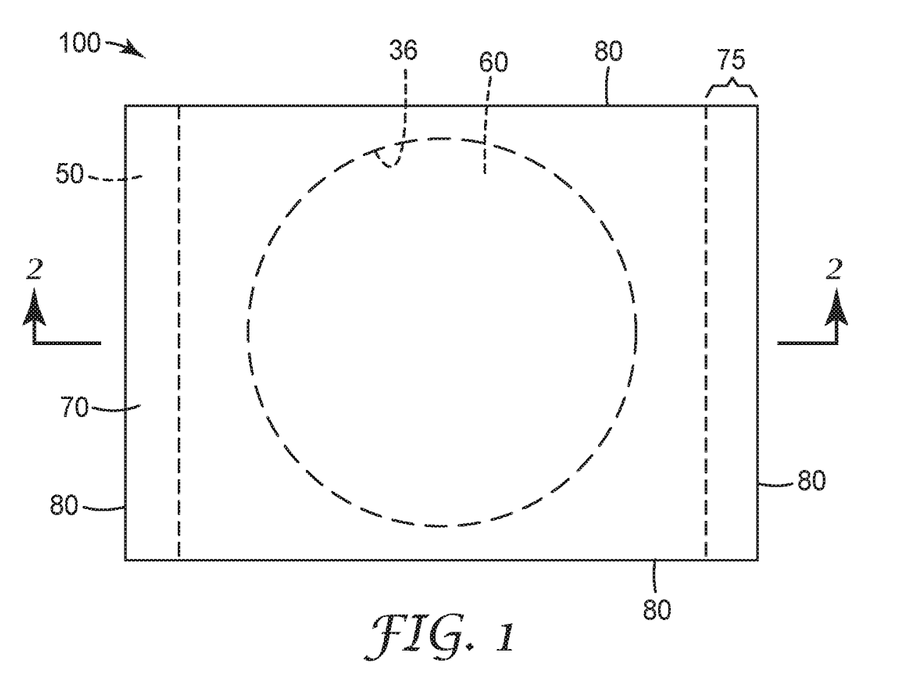
FIG. 1 is a plan view of one embodiment of a culture device according to the present disclosure.
Figure 2:
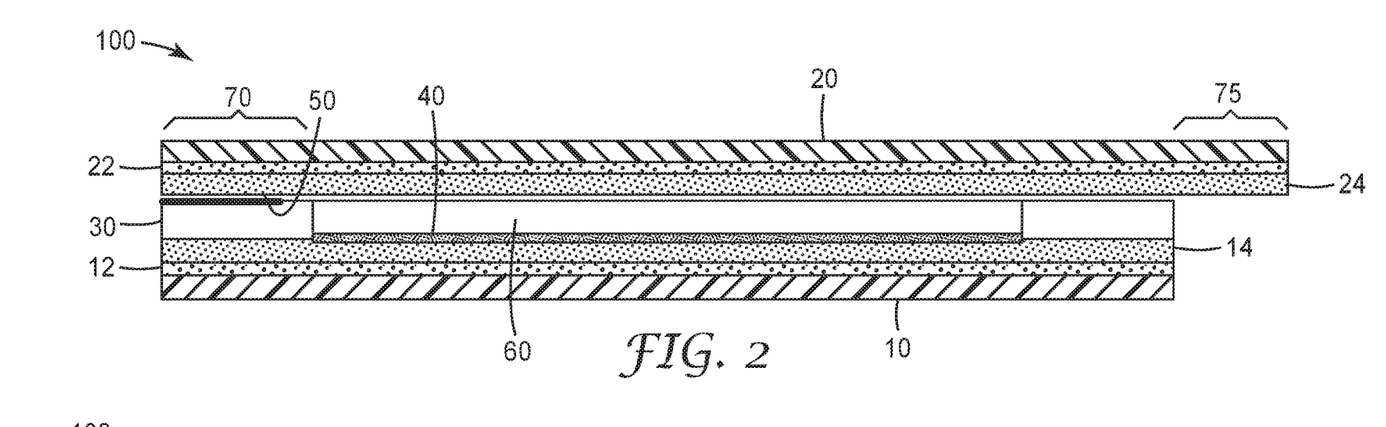
FIG. 2 is a cross-sectional side view, along line 2-2, of the culture device of FIG. 1.
Figure 3:
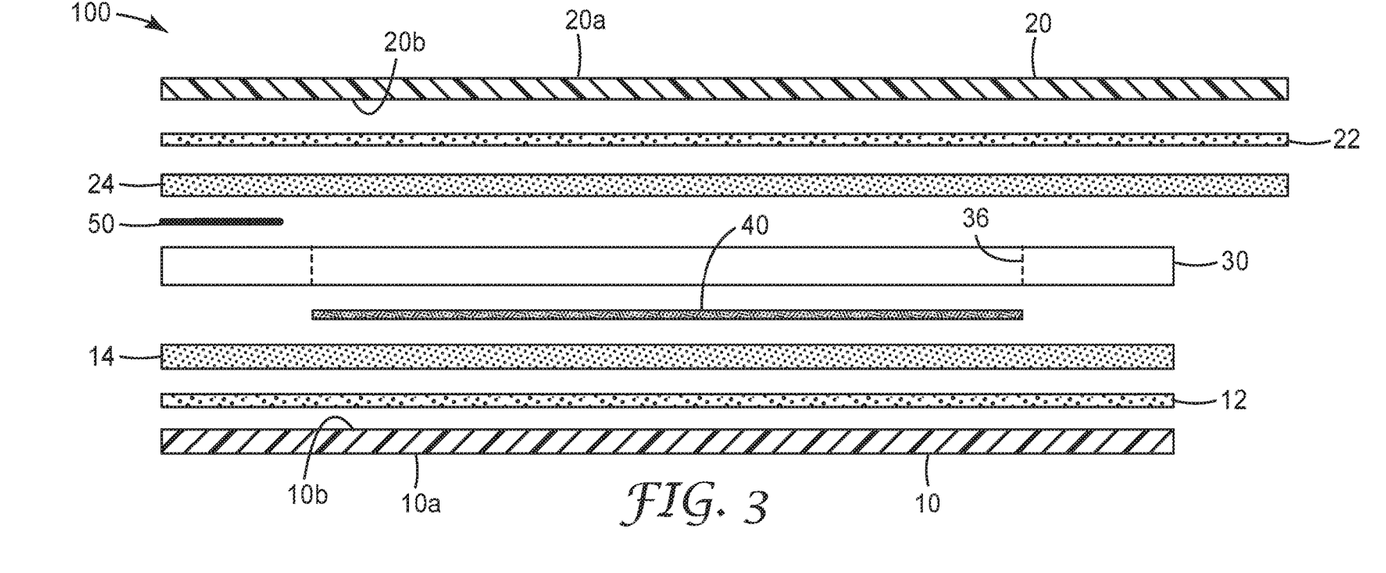
FIG. 3 is an exploded side view of the culture device of FIG. 1.

In one aspect, the present disclosure provides a culture device for culturing and detecting a Lactic Acid Bacteria (LAB). With reference to FIGS. 1-3, a culture device 100 of the present disclosure comprises a waterproof base 10, a waterproof coversheet 20, and a spacer member 30 disposed between the base 10 and coversheet 20. The base 10 has an inner surface 10b and an outer surface 10a opposite the inner surface. The coversheet 20 has an inner surface 20b and an outer surface 20a opposite the inner surface. In any embodiment, the inner surface 10b of the base 10 is disposed in facing relationship with the inner surface 20b of the coversheet 20.

Base 10 is preferably a relatively stiff waterproof film made of a material (e.g., polyester, polypropylene, or polystyrene) that will not absorb or otherwise be adversely affected by water. Base 10 preferably is made using a material that is substantially nontransmissible to gaseous oxygen. Nonlimiting examples of suitable materials for base 10 include polyester films at least about 15 µm to at least about 180 µm thick, polypropylene films at least about 100 µm to at least about 200 µm thick and polystyrene films at least about 300 µm to about 380 µm thick. Other suitable bases include ethylene vinyl alcohol copolymer films, polyvinyl alcohol films, and polyvinylidene chloride films. Base 10 can be transparent if one wishes to view colonies through the base.

The coversheet 20 is used to cover the inner surface 10b of the base 10, to define the growth compartment 60 and, optionally, to view the growth compartment during shipping, storage, incubation, and/or colony counting. Coversheet 20 is preferably a relatively stiff waterproof film made of a material (e.g., polyester, polypropylene, or polystyrene) that will not absorb or otherwise be adversely affected by water. Coversheets 20 are preferably transparent in order to facilitate the counting of colonies without opening the culture device 10, and are substantially impermeable to microorganisms and water vapor.

Generally, coversheets can be made of materials such as those used to make base 10. Coversheet 20 preferably is made using a material that is substantially nontransmissible to gaseous oxygen. Nonlimiting examples of suitable materials for base 10 include polyester films at least about 15 µm to at least about 180 µm thick, polypropylene films at least about 100 µm to at least about 200 µm thick and polystyrene films at least about 300 µm to about 380 µm thick. Other suitable bases include ethylene vinyl alcohol copolymer films, polyvinyl alcohol films, and polyvinylidene chloride films. As shown in FIG. 1, the coversheet 20 can be attached in a hinge-like fashion (e.g., using double-sided adhesive tape) along one edge of the inner surfaces of each of the base 10 and coversheet 20 to form a hinge region 70. Optionally, in any embodiment, the coversheet 20 may comprise a tab region 75 that extends beyond the base 10. The tab region 75 can be conveniently grasped when opening the device 100 to inoculate the growth compartment 60 with a sample.

A person having ordinary skill in the art will recognize the transmissibility of oxygen gas through a given type of polymer film can be reduced by increasing the thickness of the polymer film. In any embodiment, the base and coversheet of the present disclosure are polymeric films having a suitable thickness to be substantially nontransmissible to gaseous oxygen.

The spacer member 30 includes an aperture 36. The aperture 36 forms a well that serves to both define a location and thickness of a growth compartment 60 of the culture device 100. The spacer member 30, along with the base 10 and the coversheet 20, define the boundaries of the growth compartment 60. The spacer member 30 helps to confine an aqueous sample (not shown) within the growth compartment 60 during inoculation of the culture device 100.

The aperture 36 as illustrated in FIG. 1 defines a circular shape. However, it is contemplated the aperture 36 may define other shapes (e.g., square, rectangle, oval). The walls of the aperture 36 provide a well of predetermined size and shape and defines the thickness of the growth compartment 60 of the culture device 100.

The spacer member 30 should be thick enough to form a well having a predetermined volume, e.g., 1 mL, 2 mL, 3 mL, 5 mL, or 10 mL, depending on the size of the growth compartment 60 and the size of sample to be placed in the culture device. In any embodiment, spacer member 30 is made of any nonporous material that is hydrophobic (non-wetting), inert to microorganisms, and, optionally, sterilizable. In any embodiment, the spacer member 30 can be coupled (e.g., via a pressure-sensitive adhesive) directly to the base 10 or coversheet 20. Additionally or alternatively, the spacer member 30 can be coupled (e.g., via an adhesive tape 50) indirectly to the base or coversheet (e.g., the spacer member can be coupled to the first or second dry coating that is coated onto the base or coversheet, respectively).

The growth compartment 60 can be at any accessible location in the culture device 100 between the base 10 and the coversheet 20. Preferably, the growth compartment 60 is located away from the peripheral edges 80 of the device 100.

Preferably, the spacer member 30 is constructed of a nonporous material (e.g., a metal, glass, a polymeric resin) that does not substantially inhibit growth of microorganisms and does not substantially absorb water or macroscopic carbon dioxide bubbles from a hydrogel that is contacted with the spacer member. Nonlimiting examples of suitable materials from which a spacer member 30 can be made include polyolefins (e.g., polyethylene, polypropylene and the like), polyethylene terephthalate, polyurethane, polystyrene, polyvinylidene chloride, polymethyl methacrylate, polyvinylidene fluoride or other polymer films, for example.

A device of the present disclosure comprises a dry, cold-water-soluble gelling agent disposed in the growth compartment. Preferably, the gelling agent is adhered, either directly or indirectly, to the base 10 and/or the coversheet 20 of the device 100. In any embodiment, the gelling agent may be uniformly distributed onto the inner surface 10b of the base 10 and/or the inner surface 20b of the coversheet 20 in the growth compartment 60 of the device 100.

Suitable gelling agents for use in the first dry coating 24 include cold-water-soluble natural and synthetic gelling agents. Natural gelling agents such as algin, carboxymethyl cellulose, tara gum, hydroxyethyl cellulose, guar gum, locust bean gum, xanthan gum, and synthetic gelling agents such as polyacrylamide, polyurethane, polyethylene oxides, and mixtures thereof are generally suitable. Appropriate gelling agents can be selected according to the teaching of this disclosure and the disclosures of U.S. Pat. Nos. 4,565,783; 5,089,413; and 5,232,838. Preferred gelling agents include guar gum, locust bean gum, and xanthan gum; these gelling agents being useful individually, or preferably, in combination with one another.

Thus, in any embodiment, a device 100 of the present disclosure optionally can comprise a first dry coating 14 adhered to at least a portion or all of the inner surface 10b of the base 10 in the growth compartment 60. The first dry coating 14, if present, may comprise the dry, cold-water-soluble gelling agent. Optionally, a first adhesive layer 12 is adhered to the base 10 and at least a portion of the first dry coating is adhered to the first adhesive layer in the growth compartment 60.

The coversheet 20 can be free of any coating (not shown). Alternatively, if the device 100 does not have a first dry coating 14 adhered to the inner surface 10b of the base 10 in the growth compartment 60, the coversheet 20 may comprise a second dry coating 24 adhered thereto in the growth compartment. The second dry coating 24, if present, may comprise the dry, cold-water-soluble gelling agent. Optionally, a second adhesive layer 22 is adhered to the coversheet 20 and at least a portion of the second dry coating 24 is adhered to the second adhesive layer in the growth compartment 60. In any embodiment, a portion of the layer of second adhesive layer 22 may be used to facilitate sealing the coversheet 20 to at least a portion of the spacer member 30.

As regards the first and second dry coatings, the coatings optionally can comprise any nutrient or nutrient medium that is cold-water-reconstitutable, that does not substantially interfere with the cold-water gelling properties of the gelling agent, and that supports growth of an anaerobic microorganism. The particular nutrient or nutrients suitable for use in the culture device will depend on the microorganism to be grown in the device, and will be easily selected by those skilled in the art. Generally, such nutrients are cold-water soluble. Suitable nutrients for supporting bacterial growth are known in the art and include without limitation yeast extract, peptone, sugars, suitable salts, and the like. In any embodiment, the first and/or second dry coating further can comprise a selective agent (e.g., a nutrient, an antibiotic, and combinations thereof) that facilitates the growth of a particular anaerobic microorganism or group of microorganisms over another microorganism or group of microorganisms. Those skilled in the art will recognize that a variety of other formulations could be used and that these do not detract from the scope of this invention.

Preferably, when the first dry coating 14 consists primarily of dry powder or dry powder agglomerate, the first coating 14 is disposed on a first adhesive layer 12 that is disposed on at least a portion of the inner surface 10b of the base 10. The first dry coating 14 can be deposited onto the base 10 or onto the optional first adhesive layer 12 using compounding processes, adhesive coating processes, and liquid-coating processes and/or dry-coating processes described, for example, in U.S. Pat. Nos. 4,565,783; 5,089,413; and 5,232,838; which are all incorporated herein by reference in their entirety.

Preferably, when the second dry coating 24 consists primarily of dry powder or dry powder agglomerate, the second coating 24 is disposed on a second adhesive layer 22 that is disposed on at least a portion of the inner surface 20b of the coversheet 20. The second dry coating 24 can be deposited onto the coversheet 20 or onto the optional second adhesive layer 22 using compounding processes, adhesive coating processes, and liquid-coating processes and/or dry-coating processes described, for example, in U.S. Pat. Nos. 4,565,783; 5,089,413; and 5,232,838; which are all incorporated herein by reference in their entirety.

The growth compartment 60 is defined as a volume disposed between the inner surfaces (inner surfaces 10b and 20b, respectively) of the base 10 and coversheet 20, the volume encompassing at least a portion of the first dry coating 14 and/or second dry coating 24. Thus, when an aqueous liquid is distributed into the growth compartment, the aqueous liquid is in fluidic contact with at least a portion of the first dry coating 14, if present, and/or second dry coating 24, if present. The thickness of the growth compartment 60 may vary depending upon, for example, the volume of aqueous liquid (not shown) deposited in the culture device, the presence of solids (e.g., suspended particulates and/or a membrane filter) associated with the sample (not shown), and/or a spacer member 30 in the culture device 10.

Culture devices of the present disclosure further comprise an effective amount of a dry oxygen-scavenging reagent, a dry buffer system, and an effective amount of a dry carbon dioxide-generating reagent. Each of the oxygen-scavenging reagent, the buffer system, and the carbon dioxide-generating reagent is disposed in the growth compartment. "Dry", as used herein, means the reagent is substantially water-free. The phrase "substantially water-free" refers to a reagent that has a water content no greater than about the water content of the material (e.g., provided as a powder or as a dehydrated aqueous coating) once it has been permitted to equilibrate with the ambient environment.

At least one dry component (e.g., the gelling agent) is hydrated with an aqueous liquid before, during, or after the introduction (e.g., inoculation) of sample material into the growth compartment of the culture device, as described herein. Typically, the sample material and/or aqueous liquid is introduced into the growth compartment of the culture device in ambient conditions (i.e., in an aerobic gaseous environment). Thus, after inoculation of the growth compartment with a sample under aerobic conditions, the aqueous liquid in the growth compartment of the culture device comprises a first dissolved-oxygen concentration. The oxygen-scavenging reagent in the culture device functions to reduce the first dissolved-oxygen concentration in the aqueous liquid in the growth compartment to a second dissolved-oxygen concentration that is substantially lower than the first dissolved-oxygen concentration. This reduction of the dissolved oxygen concentration in the growth compartment of the inoculated culture device facilitates the growth of obligately-anaerobic or microaerotolerant LAB in the culture device.

In any embodiment, the effective amount of the oxygen-scavenging reagent is selected such that reducing the first dissolved oxygen concentration to the second dissolved oxygen concentration occurs within about 120 minutes after bringing the oxygen-scavenging reagent into fluidic contact with the predefined volume of aqueous liquid in the growth compartment of the culture device. In any embodiment, the effective amount of the oxygen-scavenging reagent is selected such that reducing the first dissolved oxygen concentration to the second dissolved oxygen concentration occurs within about 60 minutes after bringing the oxygen-scavenging reagent into fluidic contact with the predefined volume of aqueous liquid in the growth compartment of the culture device. In any embodiment, the effective amount of the oxygen-scavenging reagent is selected such that reducing the first dissolved oxygen concentration to the second dissolved oxygen concentration occurs within about 30 minutes after bringing the oxygen-scavenging reagent into fluidic contact with the predefined volume of aqueous liquid in the growth compartment of the culture device.

In any embodiment, reducing the first dissolved oxygen concentration to the second dissolved oxygen concentration occurs at a temperature between ambient temperature (e.g., about 23 degrees C.) and about 42 degrees C., inclusive. Thus, in any embodiment of a method according to the present disclosure, it is not required to incubate the culture device at an elevated temperature (i.e., above ambient temperature) in order to reduce the first dissolved oxygen concentration to the second dissolved oxygen concentration after bringing the oxygen-scavenging reagent into fluidic contact with the predefined volume of aqueous liquid in the growth compartment of the culture device.

A person having ordinary skill in the art will recognize the amount of oxygen removed from the growth compartment of a culture device of the present disclosure within a period of time suitable for culturing microorganisms is dependent inter alia upon the quantity of oxygen-scavenging reagent in the growth compartment of the culture device. Therefore, by adjusting the amount of oxygen-scavenging reagent in the growth compartment according to the present disclosure, the culture device can be configured for culturing microaerotolerant LAB or for culturing obligately anaerobic LAB.

A number of oxygen-scavenging reagents are known including, for example, ascorbic acid (e.g., L-ascorbic acid) and salts thereof, ferrous iron salts, metal salts of sulfite, bisulfite, and metabisulfite. A suitable oxygen-scavenging reagent according to the present disclosure consumes enough oxygen to create a low-oxygen or anaerobic local environment and produces quantities and types of reaction products that can be in fluidic communication with LAB without substantially inhibiting growth of the LAB. In any embodiment, the oxygen-scavenging reagent is disposed in the growth compartment in a quantity of about 1.5 micromoles/10 cm$^2$ to about 15 micromoles/10 cm$^2$.

Preferably, in any embodiment, the oxygen-scavenging reagent is provided in the form of a dry powder. More preferably, in any embodiment, the oxygen-scavenging reagent is provided as a dry powder that is milled and classified to form a population of particles with a size distribution consisting essentially of particles having a diameter of less than 106 microns. Advantageously, an oxygen-scavenging reagent provided in particles having a diameter of less than 106 microns can be adhered to the base or the coversheet (e.g., adhered to an adhesive layer coated onto the base or coversheet) in an amount effective to create and maintain (e.g., up to about 24 hours of incubation, up to about 48 hours of incubation, up to about 72 hours of incubation, up to 4 days of incubation, up to 5 days of incubation, up to 7 days of incubation, at least 24 hours of incubation, at least 48 hours of incubation, at least 72 hours of incubation, at least 4 days of incubation, at least 5 days of incubation, at least 7 days of incubation) an anaerobic environment in the growth compartment when the device is inoculated with a predefined volume of aqueous liquid and closed.

Adhesive used in the optional adhesive layer 22 disposed on the coversheet 20 can be the same as or different from the adhesive used in the optional adhesive layer 12 disposed on the base 10. In addition, the second dry coating 24 disposed on the coversheet 20 can be the same as or different from the first dry coating 14 disposed on the base 10. Coatings on coversheet 20 can cover the entire surface facing the base, but preferably cover at least a part of the inner surface 20b that defines at least a portion of the growth compartment 60 of the culture device 100.

In any embodiment, a selective agent may be disposed in the device in a dry coating or, optionally, dissolved in an adhesive layer within the growth compartment.

Optionally, a culture device of the present disclosure further comprises a means for indicating oxygen in a culture device. Preferably, the means is capable of indicating a quantity (e.g., either a predetermined threshold quantity or a relative quantity) of oxygen present in the device. Advantageously, the means can indicate whether or when the oxygen-scavenging reagent has suitably depleted the oxygen in the growth compartment of the culture device to a concentration that facilitates the growth of microaerotolerant or obligately-anaerobic LAB. Means for detecting oxygen in a culture device are known in the art and include, for example, redox dyes (e.g., methylene blue) and oxygen-quenched fluorescent dyes.

The means can be a luminescent compound that indicates the absence of oxygen inside of the device. Suitable oxygen indicators are disclosed in U.S. Pat. No. 6,689,438 (Kennedy et al.), which is incorporated herein by reference in its entirety. Luminescent compounds appropriate as indicators for a culture device of the present disclosure will display luminescence that is quenched by oxygen. More precisely, the indicators will luminesce upon exposure to their excitation frequency with an emission that is inversely proportional to the oxygen concentration. The indicator may be coated, laminated, or extruded onto another layer, or portion of another layer, within the device. Such a layer may be disposed in the growth compartment and optionally, is separated from the growth compartment by one or more other oxygen permeable layers. Suitable compounds for indicating oxygen include metallo derivatives of octaethylporphyrin, tetraphenylporphyrin, tetrabenzoporphyrin, the chlorins, or bacteriochlorins. Other suitable compounds include palladium coproporphyrin (PdCPP), platinum and palladium octaethylporphyrin (PtOEP, PdOEP), platinum and palladium tetraphenylporphyrin (PtTPP, PdTPP), camphorquinone (CQ), and xanthene type dyes such as erythrosin B (EB). Other suitable compounds include ruthenium, osmium and iridium complexes with ligands such as 2,2'-bipyridine, 1,10-phenanthroline, 4,7-diphenyl-1,10-phenanthroline and the like. Suitable examples of these include, tris(4,7,-diphenyl-1,10-phenanthroline)ruthenium (II) perchlorate, tris(2,2'-bipyridine)ruthenium(II) perchlorate, tris(1,10-phenanthroline)ruthenium(II) perchlorate, and the like.

A culture device of the present disclosure includes an effective amount of a dry, carbon dioxide-generating reagent disposed in the growth compartment. The carbon dioxide-generating reagent, when activated by contact with an aqueous liquid in the growth compartment, establishes an equilibrium of the following dissolved species: one or more salts of carbonic acid, carbonic acid, and carbon dioxide. Advantageously, the effective amount of carbon dioxide-generating reagent is sufficient to elevate the dissolved carbon dioxide to a concentration that facilitates growth of LAB. The experimental results presented herein show the relationship between the quantity of carbon dioxide-generating reagent and the increase of carbon dioxide concentration in the aqueous hydrogel in the growth compartment.

Preferably, in any embodiment, the carbon dioxide-generating reagent is provided in the form of a dry powder. More preferably, in any embodiment, the carbon dioxide-generating reagent is provided as a dry powder that is milled and classified to form a population of particles with a size distribution consisting essentially of particles having a diameter of less than 106 microns. Advantageously, in particles having a diameter of less than 106 microns can be adhered to the base or the coversheet (e.g., adhered to an adhesive layer coated onto the base or coversheet) in an amount effective to create and maintain (e.g., up to about 24 hours of incubation, up to about 48 hours of incubation, up to about 72 hours of incubation, up to 4 days of incubation, up to 5 days of incubation, up to 7 days of incubation, at least 24 hours of incubation, at least 48 hours of incubation, at least 72 hours of incubation, at least 4 days of incubation, at least 5 days of incubation, at least 7 days of incubation) a $CO_2$-enriched environment in the growth compartment when the device is inoculated with a predefined volume of aqueous liquid and closed.

A culture device of the present disclosure includes a dry buffer system disposed in the growth compartment that, when hydrated with deionized water, brings the water to a pH less than or equal to 6.35. The acidic pH provides several advantages: i) the acidic environment selectively favors growth of acid-tolerant microorganisms (e.g., LABs) over other microorganisms that may be present in a sample and ii) the acidic environment can shift the equilibrium of the carbon generating reagent toward a higher proportion of dissolved $CO_2$. Both of these advantages can facilitate growth of LABs in the culture device.

Buffer systems used in a device of the present disclosure include any microbiologically-compatible buffer having a $pK_a$ of 7.0 or less; preferably, about 6.5 or less. The acidic and basic components of the buffer system are present in the culture device in a ratio such that, when a predefined volume of deionized water is contacted with the buffer system, the pH of the in the growth compartment is less than 6.35. Suitable buffer systems include, for example, 2-(N-morpholino)ethanesulfonic acid and sodium 2-(N-morpholino)ethanesulfonic acid, and succinic acid and sodium succinate. A person having ordinary skill in the art will recognize the ratio of acid and base components of the buffer system can be adjusted in order to achieve the desired pH of the aqueous mixture formed when an predetermined volume of aqueous liquid (e.g., comprising the sample) is deposited in the growth compartment and the device is closed.

A culture device of the present disclosure optionally includes an indicator reagent. Suitable indicator reagents are useful to detect LAB. Optionally, the indicator reagent may distinguish certain LAB from other LAB or non-LAB microorganisms. Suitable indicator reagents include, for example, a pH indicator, a redox indicator, a chromogenic enzyme substrate, and a fluorogenic enzyme substrate for detecting the presence of a microorganism. A person having ordinary skill in the art will recognize indicator reagents useful for detecting LAB. The indicator should not substantially interfere with the oxygen-scavenging reagent. In any embodiment, the indicator reagent may be disposed in the device in a dry coating or, optionally, dissolved in an adhesive layer within the growth compartment.

A culture device of the present disclosure optionally includes a reducing agent. Suitable reducing reagents are useful to lower the oxidation-reduction potential of the growth medium and, thereby, facilitate growth of anaerobic LAB. Suitable reducing agents include, for example, sodium thioglycollate, L-cysteine, dithiothreitol, dithioerythritol, and combinations thereof.

In any embodiment, the growth compartment can be dimensioned to be hydrated with a 1 milliliter aqueous liquid volume. Water comprises about 0.54 μmoles of dissolved oxygen per milliliter. Thus, the first dry coating and/or second dry coating preferably comprises at least enough oxygen-scavenging reagent to consume 0.54 μmoles of oxygen in a period of 120 minutes or less at about 22 degrees C. to about 42 degrees C. More preferably, the first dry coating and/or second dry coating preferably comprises at least enough oxygen-scavenging reagent to consume more than 0.54 μmoles of oxygen in a period of 120 minutes or less at about 22 degrees C. to about 42 degrees C.

In any embodiment, the first dry coating and/or second dry coating can include any number of other components, such as dyes (e.g., a pH indicator), crosslinking agents, reagents (e.g., selective reagents or indicator reagents such as chromogenic or fluorogenic enzyme substrates), or a combination of any two or more of the foregoing components. For example, for some uses it is desirable to incorporate an indicator of microbial growth (e.g., a pH indicator, a chromogenic enzyme substrate, a redox dye) in the first and/or second dry coating or in an adhesive of to which the first and/or second dry coating is adhered. Suitable dyes include those that are metabolized by or otherwise react with the growing microorganisms, and in so doing cause the colonies to be colored or fluorescent for easier visualization. Such dyes include triphenyl tetrazolium chloride, p-tolyl tetrazolium red, tetrazolium violet, veratryl tetrazolium blue and related dyes, and 5-bromo-4-chloroindolyl phosphate disodium salt. Other suitable dyes include those sensitive to pH changes during the growth of microorganisms, such as neutral red.

For some uses it is desirable to form a dry coating that, when reconstituted with an aqueous liquid, forms a hydrogel that is stiff enough to allow inoculation by streaking. To form streakable medium, an effective amount of a suitable cross-linking agent can be incorporated into one or more dry coating that includes a gelling agent. Suitable cross-linking agents do not substantially affect the growth of the intended microorganisms. Suitable types and amounts of cross-linking agents are easily selected by those skilled in the art. For example, with guar gum, cross-linking agents such as potassium tetraborate, aluminum salts, or calcium salts are suitable, and can be added in effective amounts, e.g., less than about 1.0 percent by weight of dry coating.

At least one dry coating can optionally include reagents necessary for carrying out certain microbiological tests. For example, antibiotics can be included for carrying out antibiotic susceptibility tests. For microorganism identification, differential reagents that undergo a color change in the presence of a particular type of microorganism can be included.

In any embodiment, the dry buffer system, the reducing agent, the carbon-dioxide-generating reagent and/or the indicator reagent can be disposed in the growth compartment as a dry powder (e.g., dry powder 40 of FIGS. 2 and 3) that is not adhered to the first or second adhesive layers. Alternatively, the the dry buffer system, the reducing agent, the carbon-dioxide-generating reagent and/or the indicator reagent can be including in the first and/or second coatings as described herein.

A culture device of the present can be prepared using a variety of techniques. Generally, a device can be made by hand or with common laboratory equipment as described herein and in U.S. Pat. Nos. 4,565,783; 5,089,413; and 5,232,838, for example.

A nonlimiting example of a suitable pressure-sensitive adhesive that can be used in the first adhesive layer and/or second adhesive layer is a copolymer of 2-methylbutylacrylate/acrylic acid in a mole ratio of 90/10. Other preferred pressure sensitive adhesives that can be used include isooctylacrylate/acrylic acid in a mole ratio of 95/5 or 94/6 and silicone rubber. Adhesives that turn milky (e.g., opaque) upon exposure to water are less preferred, but can be used in conjunction with a non-transparent base or in situations where colony visualization is not required. Heat-activated adhesives having a lower melting substance coated onto a higher melting substance and/or water-activated adhesives such as mucilage are also known and can be used in this invention. When incorporating an indicator reagent as described above in order to facilitate visualization of colonies, it is generally preferred to incorporate the indicator reagent in the adhesive or broth coating mixture, rather than in the powder.

The first adhesive layer or second adhesive layer is coated (e.g., using a knife coater) onto the top surface of base or coversheet to form an adhesive layer at a thickness that is preferably less than the average diameter of the particles of dry powder or agglomerated powder to be adhered to the adhesive. Generally, enough adhesive is coated in order to adhere the particles to the substrate (e.g., the first or coversheet described herein) but not so much that the particles become completely embedded in the adhesive. Generally, an adhesive layer about 5 μm to about 12 μm thick is suitable.

Preferably, when gelling agent is included in the first dry coating and/or second dry coating, it is included in an amount such that a predetermined quantity of water or an aqueous sample, e.g., 1 to 3 ml, placed in the growth compartment will form a hydrogel having a suitable viscosity, e.g., about 1500 cps or more when measured at 60 rpm with a Brookfield Model L VF viscometer at 25° C. Hydrogels of this viscosity allow convenient handling and stacking of the culture devices during incubation and provide for distinct colony formation in the medium. For instance, 0.025 g to 0.050 g of powdered guar gum spread substantially uniformly over a surface area of 20.3 cm$^2$ will provide a sufficiently viscous medium when reconstituted with 1 to 3 ml of an aqueous sample. The size of the powder particles can be used to control the coating weight per unit area. For example, under conditions where a 100 mesh guar gum coats to a weight of about 0.05 g/20.3 cm$^2$, a 400 mesh guar gum coats to a weight of about 0.025 g/20.3 cm$^2$.

In any embodiment, the first dry coating or second dry coating can comprise one or more nutrients to facilitate growth of microorganisms. When the coating consists essentially of powders or powder agglomerates, the preferred ratio of gelling agent to nutrient in an adhered powder medium is determined by the particular microorganism to be grown on the device. For general purposes, however, a ratio from about 4 to 1 to about 5 to 1 (total gelling agent to total nutrient, based on weight) is preferred. The powder in an adhered powder medium can be applied to the adhesive layer (e.g., first adhesive layer 12 and/or second adhesive layer 22) by any means suitable for the application of a substantially uniform layer. Examples of suitable methods to apply the layer of powders include the use of a shaker-type device, or the use of a powder coater.

Suitable nutrients for use in a device of the present disclosure include those found in culture medium for growing and detecting LAB. Non-limiting examples of suitable nutrients include a source of peptone (e.g., meat extract, meat peptone), yeast extract, an enzymatic digest of casein, and a carbohydrate (e.g., maltose, glucose, trehalose, sucrose). Preferably, the carbohydrate is present in the device in an amount that is high enough to facilitate growth (biomass production) of LAB and fermentation by LAB to lactic acid or other metabolites (e.g., $CO_2$) that can be used to detect LAB colonies.

When using culture device of the present disclosure, an accurate count of the colonies of microorganisms present can be desirable. Thus, in any embodiment, a culture device of the present disclosure may comprise a grid pattern on base or, alternatively, on the coversheet. The grid pattern may comprise a square grid pattern such as, for example, the square grid pattern disclosed in U.S. Pat. No. 4,565,783. The grid pattern may be produced on the first or coversheet by any suitable process such as printing methods, for example.

In another aspect, the present disclosure provides a method of making a self-contained anaerobic environment-generating culture device. The method comprises adhering a cold water-soluble gelling agent onto a portion of a base. The gelling agent may be dry (e.g., in the form of substantially water-free particles) when adhered to the base or the gelling agent may be adhered to the base as a liquid coating (e.g., an aqueous liquid coating) and subsequently dried to a substantially water-free state. The method further comprises positioning the base adjacent a coversheet and placing a spacer member therebetween, the spacer member comprising an aperture that defines a growth compartment as described herein. In any embodiment, the spacer member may be attached (e.g., via an adhesive) to the base or the cover sheet.

The base is positioned adjacent the cover sheet such that at least a portion of the adhered gelling agent faces the growth compartment disposed between the base and the coversheet. Optionally, in any embodiment, a first adhesive layer may be applied (e.g., using coating processes known in the art) to the base and the cold water-soluble gelling agent may be adhered to the first adhesive layer.

In an alternative embodiment, the cold water-soluble gelling agent may be adhered to the coversheet by any of the processes described for adhering the gelling agent to the base. Drying the adhered gelling agent, if the gelling agent is liquid-coated, can be performed by a number of processes known in the art. The coating can be dried in an oven (e.g., a gravity oven, a convection oven), for example, according to the process described in U.S. Pat. No. 5,601,998, which is incorporated herein by reference in its entirety. Preferably, the adhered gelling agent is dried until it is substantially water-free. As used herein, the phrases "substantially dry", "substantially water-free" or the like refer to a coating which has a water content no greater than about the water content of the dehydrated coating once it has been permitted to equilibrate with the ambient environment.

The method further comprises depositing the oxygen-scavenging reagent, the buffer system, and the carbon dioxide-generating reagent into the growth compartment of the culture device. In any embodiment, any one or all of the oxygen-scavenging reagent, the buffer system, and the carbon dioxide-generating reagent can be deposited into the growth compartment as a dry powder. Optionally, any one or all of oxygen-scavenging reagent, the buffer system, and the carbon dioxide-generating reagent may be adhered to an adhesive (e.g. a first adhesive layer or second adhesive layer as described herein) in the growth compartment. Other optional components (e.g., indicator reagents, selective agents, nutrients) may also be deposited into the growth compartment, optionally, adhered to an adhesive layer.

Positioning the base adjacent the coversheet, such that the adhered gelling agent faces the growth compartment disposed between the base and the coversheet can be performed in a variety of ways. A representative example of positioning the base and coversheets adjacent each other so that a portion of the gelling agent overlaps the growth compartment is shown in FIGS. 1-3. It can be seen that the overlapping configuration permits an operator to deposit an aqueous liquid between the base and the coversheet thereby placing the gelling agent, the oxygen-scavenging reagent, the buffer system, and the carbon dioxide-generating reagent into fluid communication.

In yet another aspect, the present disclosure provides a method of detecting a microorganism. The method uses any embodiment of the culture device of the present disclosure described above. The culture device comprises a base; a coversheet; a spacer member disposed between the inner surfaces of the base and the coversheet, the spacer member comprising an aperture that defines a shape and a depth of a growth compartment; a dry, cold-water-soluble gelling agent adhered to the base or the coversheet in the growth compartment; and an effective amount of a dry oxygen-scavenging reagent, a dry buffer system, and an effective amount of a dry carbon dioxide-generating reagent, each disposed in the growth compartment as described herein.

In any embodiment, the method comprises opening the culture device to provide access to the growth compartment therein, placing a predefined volume of aqueous liquid into the growth compartment, placing a sample into the growth compartment, closing the culture device, incubating the culture device for a period of time sufficient to permit formation of a microbial colony in the culture medium, and detecting the microbial colony, wherein placing the aqueous liquid and the sample into the growth compartment and closing the culture device comprises forming a semi-solid microbial culture medium enclosed by the base, the coversheet, and the spacer of the culture device; the culture medium having a pH between 4.0 and 6.35.

In any embodiment, the predetermined volume of aqueous liquid used to hydrate and/or inoculate the culture device is about 0.1 milliliter to about 10 milliliters. In any embodiment, the predetermined volume of aqueous liquid used to hydrate and/or inoculate the culture device is about 1 milliliter. In any embodiment, the predetermined volume of aqueous liquid used to hydrate and/or inoculate the culture device is about 2 milliliters. In any embodiment, the predetermined volume of aqueous liquid used to hydrate and/or inoculate the culture device is about 3 milliliters. In any embodiment, the predetermined volume of aqueous liquid used to hydrate and/or inoculate the culture device is about 4 milliliters. In any embodiment, the predetermined volume of aqueous liquid used to hydrate and/or inoculate the culture device is about 5 milliliters. In any embodiment, the predetermined volume of aqueous liquid used to hydrate and/or inoculate the culture device is about 10 milliliters. In any embodiment, the aqueous liquid used to hydrate the growth region of the culture device is distributed over an area that results in approximately one milliliter of liquid per 20.3 $cm^2$ of growth region.

In any embodiment of the method, placing the predetermined volume into the growth compartment comprises simultaneously placing the sample into the growth compartment. For example, the sample may be a liquid (e.g., a water or beverage sample to be tested for microbial contamination) or the sample may be a solid or semisolid sample suspended in a liquid carrier or diluent.

Alternatively, in any embodiment, placing the predetermined volume into the growth compartment does not comprise simultaneously placing the sample into the growth compartment. For example, the sample may comprise a liquid, a solid, or a semisolid material that is placed into the growth compartment before or after a predefined volume of (preferably sterile) liquid carrier or diluent is placed into the growth compartment of the culture device.

Typically, the culture device is placed on a generally-level surface and the base and coversheet are separated (e.g., the coversheet is lifted) to provide access to the growth compartment of the culture device while the growth compartment is being hydrated and/or inoculated. Advantageously, the culture device can be hydrated and/or inoculated in an aerobic environment (i.e., in air). Typically, an aqueous liquid (which may include sample material to be tested) used to hydrate the device is pipetted onto the growth compartment between the base and the coversheet. After the predefined volume of aqueous liquid is deposited into the growth compartment, the culture device is closed (e.g., by lowering the coversheet until it contacts the spacer member). Optionally, a flat or concave spreader, similar to those used to inoculate PETRIFILM culture devices, can be used to distribute the aqueous liquid over a predefined area within the culture device.

In any embodiment of the method, placing the predetermined volume into the growth compartment can comprise simultaneously placing the sample into the growth compartment. In these embodiments, the sample may comprise an aqueous liquid and/or the sample may be diluted into or suspended in an aqueous liquid.

Alternatively, in any embodiment, placing the predetermined volume into the growth compartment does not comprise simultaneously placing the sample into the growth compartment. In these embodiments, a predetermined volume of aqueous liquid can be placed (e.g., pipetted) into the growth compartment before or after placing the sample into the growth compartment. For example, the sample may be captured onto a membrane filter, which is placed into the growth compartment before or after the gelling agent is hydrated with aqueous liquid.

In any embodiment of the method, placing the sample into the growth compartment comprises placing one or more additive into the growth compartment. The one or more additive can be placed into the growth compartment with the sample or separately. The one or more additive may perform a variety of functions in the method. For example, in any embodiment, the one or more additive may comprise a nutrient (e.g., a dry nutrient) or a nutrient medium (e.g., a dry nutrient medium) to facilitate growth of LAB in the device. Such nutrients and nutrient media are well known in the art and may be selected based upon the particular microorganism to be cultured. The nutrient and nutrient medium should not substantially interfere with the oxygen-scavenging reagent. This can be tested readily by using an oxygen sensor (e.g., a Planar Oxygen Sensor, 5 mm diameter, Part Number 200000023; obtained from Presens Precision Sensing GmnH; Regensburg, DE) as described in Examples 2-3 of PCT Publication No. WO2015/061213, which is incorporated herein by reference in its entirety.

Alternatively or additionally, in any embodiment, the additive comprises one or more selective agent (e.g., an antibiotic, a salt) that favors growth of one microorganism over at least one other microorganism. In an embodiment, the selective agent favors the growth of LAB over non-LAB microorganisms. Alternatively or additionally, in any embodiment, the additive comprises an indicator reagent (e.g., a pH indicator, a redox indicator, a chromogenic enzyme substrate, a fluorogenic enzyme substrate) for detecting the presence of a microorganism. A person having ordinary skill in the art will recognize selective agents and indicator reagents useful for detecting LAB. The selective agent and/or indicator should not substantially interfere with the oxygen-scavenging reagent. This can be tested readily by using an oxygen sensor as described above.

In any embodiment, an effective amount of the selective agent substantially permits germination and growth of Lactic Acid Bacteria in the culture device and the effective amount of selective agent substantially inhibits growth of *E. coli*, *S. aureus*, *C. sporogenes*, *C. perfringens*, *Bacteroides fragilis*, *Prevotella melaninogencia*, and/or *Fusobacterium* species.

When contacted by aqueous liquid in the growth compartment; the dry components (e.g., the oxygen-scavenging reagent, the buffer system, the carbon-dioxide-generating reagent, the nutrient, the indicator reagent, the reducing agent, and/or the selective agent) and aqueous liquid form a mixture that comprises a first concentration of dissolved oxygen and a first concentration of dissolved carbon dioxide.

In any embodiment, the first concentration of dissolved oxygen in the aqueous mixture in the growth compartment may be a concentration that substantially inhibits growth of an obligately-anaerobic microorganism, a microaerophilic microorganism, and/or a microaerotolerant microorganism. In these embodiments, placing the components in aqueous fluid communication initiates an oxygen-scavenging reaction, thereby reducing the first concentration of dissolved oxygen in the aqueous liquid in the growth compartment to a second concentration that is lower than the first concentration (e.g., at least about 25% lower, at least about 50% lower, at least about 60% lower, at least about 70% lower, at least about 80%, at least about 90%, at least about 95%, at least about 98%, at least about 99% lower, or greater than 99% lower than the first concentration).

In any embodiment, reducing the first concentration of dissolved oxygen to the second concentration of dissolved oxygen can comprise reducing the dissolved oxygen in the aqueous mixture in the growth compartment to a second concentration that is low enough to support the growth of LAB (e.g., aerotolerant LAB or obligately anaerobic LAB).

In any embodiment, reducing the first concentration of dissolved oxygen to the second concentration of dissolved oxygen comprises reducing the dissolved oxygen to the second concentration in the aqueous mixture in the growth compartment in less than or equal to about 120 minutes after the mixture is formed. In any embodiment, reducing the first concentration of dissolved oxygen to the second concentration of dissolved oxygen comprises reducing the dissolved oxygen to the second concentration in the aqueous mixture in the growth compartment in less than or equal to about 90 minutes after the mixture is formed. In any embodiment, reducing the first concentration of dissolved oxygen to the second concentration of dissolved oxygen comprises reducing the dissolved oxygen to the second concentration in the aqueous mixture in the growth compartment in less than or equal to about 60 minutes after the mixture is formed. In any embodiment, reducing the first concentration of dissolved oxygen to the second concentration of dissolved oxygen comprises reducing the dissolved oxygen to the second concentration in the aqueous mixture in the growth compartment in less than or equal to about 45 minutes after the mixture is formed. In any embodiment, reducing the first concentration of dissolved oxygen to the second concentration of dissolved oxygen comprises reducing the dissolved oxygen to the second concentration in the aqueous mixture in the growth compartment in less than or equal to about 30 minutes after the mixture is formed.

In any embodiment, the first concentration of dissolved carbon dioxide in the aqueous mixture in the growth compartment may be a concentration that supports growth of a microorganism. In these embodiments, placing the components in aqueous fluid communication initiates a carbon dioxide-generating reaction, thereby increasing the first concentration of available carbon dioxide in the aqueous mixture in the growth compartment to a second concentration (e.g., within <90 minutes, within <60 minutes, or within <30 minutes) that is higher (e.g., about 2-times the first concentration, about 4-times the first concentration, about 5-times the first concentration, about 9.4-times the first concentration) than the first concentration, as shown in the Examples. The additional available carbon dioxide does not result in the formation of macroscopic (i.e., ≥1 mm-diameter gas bubbles) in the hydrogel formed in the growth compartment when a culture device of the present disclosure is inoculated and incubated.

If the culture device is hydrated before sample material is placed into the device, the cold-water-soluble gelling agent optionally may be permitted to hydrate and form gel (e.g., at room temperature) for several minutes up to about 30 minutes or more before the device is reopened to inoculate with the culture material. During the period in which the gelling agent is permitted to hydrate and form a gel, the oxygen-scavenging reagent reduces the concentration of dissolved oxygen in the hydrated gelling agent from a first concentration to a second concentration that facilitates growth of microaerotolerant or obligately-anaerobic LAB, as discussed herein.

Before or after the growth compartment of the culture device is hydrated, sample material can be contacted with the growth compartment in a variety of ways that are known in the art. In any embodiment, the sample material is contacted with the growth area by depositing the sample material into the growth area. This can be done, for example, by pipetting, by contacting the growth compartment with a swab that was used to obtain the sample material (e.g., by swabbing a surface), by contacting the growth compartment with an inoculating loop or needle (e.g., using a streak-plate technique), or by placing a sample capture device (e.g., a swab, sponge, or membrane filter) directly into the growth compartment and re-closing the culture device. After the sample is deposited and the culture device is re-closed (taking care not to entrap macroscopically-visible air bubbles in the culture device), the oxygen-scavenging reagent resumes depletion of the dissolved oxygen in the growth compartment.

In any embodiment, after the dry components in the growth compartment of the culture device are hydrated and the gelling agent forms a gel, the culture device can be used as a contact plate (e.g., a Rodac plate). Thus, after the gel has formed, the base and the coversheet of the culture device are separated, exposing the hydrated gel. The hydrated gel is contacted with a surface to be sampled, and the culture device is re-closed, taking care not to entrap macroscopically-visible air bubbles in the culture device. Reclosing the device returns the hydrated gel to the growth compartment inside the culture device. Advantageously, the contact plate procedure can be performed in an aerobic environment and, after re-closing the culture device, a reduced-oxygen environment can be re-established in the culture device by the oxygen-scavenging reagent.

In any embodiment of the method, after the sample is placed into the growth compartment and closed, the culture device is incubated for a period of time (e.g., a predetermined period of time). The incubation conditions (e.g., the incubation temperature) can affect the rate of growth of the LAB, as is well known by a person having ordinary skill in the art. For example, incubation at lower temperatures (e.g., about 25° C.) can allow for the detection of psychrotrophic LAB. Incubation at higher temperatures (e.g., about 30° C., about 32° C., about 35° C., about 37° C.) may facilitate faster growth of certain mesophilic LAB.

In some embodiments, after inoculation, the culture device can be incubated for at least about 16 hours, at least about 18 hours, at least about 24 hours, or at least about 48 hours. In some embodiments, the culture device can be incubated not more than about 24 hours, not more than about 48 hours, or not more than about 72 hours. In certain preferred embodiments, the culture device is incubated about 24 hours to about 48 hours. In any embodiment, the culture device can be incubated, and maintain a reduced-oxygen environment therein, for about 72 hours, for about 96 hours, for about 120 hours, for about 7 days, or for about 8 days before detecting or counting LAB colonies growing in the growth compartment. In any embodiment, incubating the culture device for a period of time sufficient to permit formation of a microbial colony comprises incubating the culture device for the period of time in an aerobic atmosphere (i.e., the culture device is not placed into a reduced-oxygen container or glove box for incubation).

After the inoculated culture device is incubated, the method further comprises detecting a microbial colony. Microbial colonies can be detected in the culture device by a variety of techniques that are known in the art. After a suitable incubation period, the absence of a microorganism can be detected in a culture device by the absence of observable colonies, the absence of a change in a growth indicator (e.g., a pH indicator, a chromogenic enzyme substrate, a redox indicator such as TTC, a fluorogenic enzyme substrate) and the absence of gas bubbles associated with the metabolism of the fermentable carbohydrate in the growth medium.

An acid zone associated with a colony of microorganisms can be detected visually and/or by the use of an imaging system. For example, in a method wherein the culture medium comprises bromcresol purple as a pH indicator, the culture medium will have a purple or gray appearance at about a neutral pH. As the microorganisms grow and ferment a carbohydrate (e.g., glucose) in the culture medium, the bromcresol purple indicator will appear yellow adjacent the growing bacterial colonies. For example, in a method wherein the culture medium comprises chlorophenol red as a pH indicator, the culture medium will have a red or violet appearance at about a neutral pH. As the microorganisms and ferment a carbohydrate in the culture medium, the chlorophenol red indicator will appear yellow adjacent the growing microbial colonies.

Gas bubbles, if present in the growth compartment and associated with a colony of microorganisms (e.g., either touching the colony or within a distance of about 1 mm or less from the colony), can be detected visually and/or by the use of an imaging system. The gas bubbles may be associated with a visible colony and/or an acid zone detectable by a change in the color of a pH indicator in a region adjacent the colony of microorganisms. The gas bubble may comprise carbon dioxide generated by anaerobic fermentation of a carbohydrate, for example.

In any of the above embodiments, the method further can comprise obtaining an image of the culture device. In these embodiments, detecting the presence or absence of a LAB comprises displaying, printing, or analyzing the image of the culture device. The imaging system comprises an imaging device and may comprise a processor. In some embodiments, the imaging device can comprise a line-scanner or an area scanner (e.g., a camera). The imaging device can include a monochromatic (e.g., black-and-white) or a polychromatic (e.g., color) scanner. Advantageously, monochromatic imaging systems can provide higher resolution images, which may improve the accuracy of the result and/or reduce the time necessary to detect the presence of microorganisms in the culture device.

In some embodiments, the imaging system further comprises an illumination system. The illumination system may include at least one source of broad-spectrum visible light (e.g., a "white" light). In some embodiments, the illumination system may include at least one source of narrow-spectrum visible light (e.g., a light-emitting diode that emits a relatively narrow bandwidth of visible light such as, for example, red, green, or blue light). In certain embodiments, the illumination system may include a source of narrow-spectrum visible light (e.g., a light-emitting diode) with a light emission peak at a preselected wavelength (e.g., about 525 nm).

The image can be obtained from light reflected by the components (e.g., microbial colonies, growth media, and indicators) in the growth compartment of the culture device or the image can be obtained from light transmitted through the components in the growth compartment of the culture device. Suitable imaging systems and corresponding illumination systems are described, for example, in International Patent Publication No. WO 2005/024047 and U.S. Patent Application Publication Nos. US 2004/0101954 and US 2004/0102903, each of which is incorporated herein by reference in its entirety. Non-limiting examples of suitable imaging systems include PETRIFILM Plate Reader (PPR), available from 3M Company (St. Paul, Minn.), the PETRISCAN Colony Counter available from Spiral Biotech (Norwood, Mass.), and PROTOCOL and ACOLYTE plate scanners available from Synbiosis (Cambridge, U.K.).

In some embodiments, obtaining an image comprises obtaining a wavelength-biased image. For example, the imaging system can include a bias filter that biases the light collected by the imaging device. Filter elements are known in the art and include both "cut-off" filters (i.e., filters that allow the passage of light wavelengths either above or below a certain specified wavelength) and "band-pass" filters (i.e., filters that allow the passage of light wavelengths between certain specified upper and lower limits). A bias filter can be positioned between the illumination source and the culture device. Alternatively or additionally, a bias filter can be positioned between the culture device and the imaging device.

Exemplary Embodiments

Embodiment A is a culture device for enumerating colonies of a target microorganism, the device comprising:

a base having opposing inner and outer surfaces;

a coversheet having opposing inner and outer surfaces;

a nonporous spacer member disposed between the base and the cover sheet, wherein the spacer member is coupled to the base or the coversheet, wherein the spacer member comprises an aperture that defines a shape and a depth of a growth compartment, wherein the spacer member and the growth compartment are disposed between the inner surface of the base and the inner surface of the coversheet;

an effective amount of a dry oxygen-scavenging reagent disposed in the growth compartment, wherein the oxygen-scavenging reagent consists essentially of particles having a diameter of less than 106 microns;

a dry, cold-water-soluble gelling agent disposed in the growth compartment, wherein the gelling agent is adhered to the base or the coversheet in the growth compartment;

a dry buffer system disposed in the growth compartment that, when the growth compartment is hydrated with a predetermined volume of deionized water, forms an aqueous mixture with a pH less than or equal to 6.35; and an effective amount of a dry carbon dioxide-generating reagent disposed in the growth compartment, wherein the carbon dioxide-generating reagent consists essentially of particles having a diameter of less than 106 microns.

Embodiment B is the culture device of Embodiment A, wherein the oxygen-scavenging reagent consists essentially of particles having a diameter of less than 106 microns.

Embodiment C is the culture device of Embodiment A or Embodiment B, wherein the carbon dioxide-generating reagent consists essentially of particles having a diameter of less than 106 microns.

Embodiment D is the culture device of any one of the preceding Embodiments, further comprising a dry nutrient disposed in the growth compartment, the nutrient selected to facilitate growth of the target microorganism.

Embodiment E is the culture device of Embodiment D, wherein the nutrient comprises a fermentable carbohydrate.

Embodiment F is the culture device of Embodiment E, wherein the carbohydrate is selected from the group consisting of glucose, maltose, sucrose, and trehalose.

Embodiment G is the culture device of any one of the preceding Embodiments, further comprising a first indicator reagent disposed in the growth compartment, the first indicator reagent selected for detecting growth of the target microorganism.

Embodiment H is the culture device of any one of the preceding Embodiments, further comprising an effective amount of a selective agent disposed in the growth compartment, the selective agent selected to inhibit growth of a non-target microorganism.

Embodiment I is the culture device of Embodiment H, wherein the selective agent is selected from the group consisting of cycloheximide, a macrolide polyene, amphotericin B, natamycin, and filipin.

Embodiment J is the culture device of any one of the preceding Embodiments, further comprising an effective amount of a reducing agent disposed in the growth compartment.

Embodiment K is the culture device of Embodiment J, wherein the reducing agent is selected from the group consisting of sodium thioglycolate, dithiothreitol, and dithioerythritol.

Embodiment L is the culture device of any one of the preceding Embodiments, wherein the oxygen-scavenging reagent is adhered to the base or the coversheet in the growth compartment.

Embodiment M is the culture device of any one of the preceding Embodiments, wherein a component of the buffer system is adhered to the base or the coversheet in the growth compartment.

Embodiment N is the culture device of any one of the preceding Embodiments, wherein the buffer system comprises a component selected from the group consisting of 2-(N-morpholino)ethanesulfonic acid and sodium 2-(N-morpholino)ethanesulfonic acid, and succinic acid and sodium succinate.

Embodiment O is the culture device of any one of the preceding Embodiments, wherein the carbon dioxide-generating reagent is adhered to the base or the coversheet in the growth compartment.

Embodiment P is the culture device of any one of the preceding Embodiments, wherein the carbon dioxide-generating reagent comprises a metal carbonate.

Embodiment Q is the culture device of Embodiment P, wherein the metal carbonate is selected from the group consisting of sodium bicarbonate and sodium carbonate.

Embodiment R is the culture device of any one of Embodiments D through K, wherein the nutrient is adhered to the base or the coversheet in the growth compartment.

Embodiment S is the culture device of any one of Embodiments G through R, wherein the first indicator reagent is adhered to the base or the coversheet in the growth compartment.

Embodiment T is the culture device of any one of Embodiment H through S, wherein the selective agent is adhered to the base or the coversheet in the growth compartment.

Embodiment U is the culture device of any one of Embodiments I through T, wherein the reducing agent is adhered to the base or the coversheet in the growth compartment.

Embodiment V is the culture device of any one of the preceding Embodiments:

wherein the inner surface of the base has a first adhesive adhered thereto;

wherein one or more first component disposed in the growth compartment is adhered to the first adhesive;

wherein the first component is selected from the group consisting of the gelling agent, the oxygen-scavenging reagent, the buffer system, the nutrient, the indicator reagent, the selective agent, the reducing agent, and a combination of any two or more of the foregoing first components.

Embodiment W is the culture device of Embodiment V:

wherein a second component is disposed in the first adhesive;

wherein the second component is selected from the group consisting of the indicator reagent, the selective agent, and combinations thereof.

Embodiment X is the culture device of any one of the preceding Embodiments:

wherein the inner surface of the coversheet has a second adhesive adhered thereto;

wherein one or more third component disposed in the growth compartment is adhered to the second adhesive;

wherein the third component is selected from the group consisting of the gelling agent, the oxygen-scavenging reagent, the buffer system, the nutrient, the indicator reagent, the selective agent, the reducing agent, and a combination of any two or more of the foregoing third components.

Embodiment Y is the culture device of Embodiment X:

wherein a fourth component is disposed in the second adhesive;

wherein the fourth component is selected from the group consisting of the indicator reagent, the selective agent, and combinations thereof.

Embodiment Z is the culture device of any one of the preceding Embodiments, wherein the carbon dioxide-generating reagent comprises a salt of carbonic acid.

Embodiment AA is the culture device of any one of the preceding Embodiments, wherein the oxygen-scavenging reagent comprises ferrous iron or a salt thereof or ascorbic acid or a salt thereof.

Embodiment AB is the culture device of any one of the preceding Embodiments, further comprising a second indicator reagent disposed in fluid communication with the growth compartment, wherein the second indicator reagent indicates a presence of non-target microorganisms and the target microorganism.

Embodiment AC is the culture device of any one of the preceding Embodiments, wherein the oxygen-scavenging reagent is disposed in the growth compartment in a quantity of about 1.5 micromoles/10 $cm^2$ to about 15 micromoles/10 $cm^2$ surface area of the base or the coversheet in the growth compartment.

Embodiment AD is the culture device of any one of the preceding Embodiments, wherein the carbon dioxide-generating reagent is disposed in the growth compartment in a quantity of about 1 micromoles/10 $cm^2$ to about 15 micromoles/10 $cm^2$ surface area of the base or the coversheet in the growth compartment.

Embodiment AE is a method of detecting a microorganism in a sample, the method comprising:

opening the culture device of any one of the preceding claims to provide access to the growth compartment therein;

placing a predefined volume of aqueous liquid into the growth compartment;

placing a sample into the growth compartment;

closing the culture device;

wherein placing the aqueous liquid and the sample into the growth compartment and closing the culture device comprises forming a semi-solid microbial culture medium enclosed by the base, the coversheet, and the spacer of the culture device; the culture medium having a pH between 4.0 and 6.35;

incubating the culture device for a period of time sufficient to permit formation of a microbial colony in the culture medium; and detecting the microbial colony.

Embodiment AF is the method of Embodiment AE, wherein placing the predetermined volume into the growth compartment comprises simultaneously placing the sample into the growth compartment.

Embodiment AG is the method of Embodiment AE, wherein placing the predetermined volume into the growth compartment does not comprise simultaneously placing the sample into the growth compartment.

Embodiment AH is the method of Embodiment AG, wherein placing the sample into the growth compartment occurs after placing the predetermined volume into the growth compartment.

Embodiment AI is the method of Embodiment AG, wherein placing the sample into the growth compartment occurs before placing the predefined volume into the growth compartment.

Embodiment AJ is the method of any one of Embodiments AE through AI, wherein placing the sample into the growth compartment comprises placing an additive into the growth compartment.

Embodiment AK is the method of any one of Embodiments AE through AJ, wherein placing the additive into the growth compartment comprise placing an effective amount of a selective agent or an indicator.

Embodiment AL is the method of Embodiment AK, wherein the effective amount of the selective agent substantially permits growth of Lactic Acid Bacteria in the culture device and the effective amount of selective agent substantially inhibits growth of *E. coli, S. aureus, C. sporogenes, C. perfringens, Bacteroides fragilis, Prevotella melaninogencia*, and/or *Fusobacterium* species.

Embodiment AM is the method of any one of Embodiments AE through AL, wherein incubating the culture device for a period of time comprises incubating the culture device for the period of time in an aerobic atmosphere.

Embodiment AN is the method of any one of Embodiments AE through AM wherein, after incubating the culture device, detecting the microbial colony further comprises enumerating one or more optically-detectable colonies in the culture device.

Embodiment AO is the method of any one of Embodiments AE through AN, wherein the culture device comprises the indicator reagent disposed in the growth compartment, wherein detecting the microbial colony comprises detecting an optical change associated with the indicator reagent, wherein the optical change is detected proximate the microbial colony.

Embodiment AP is the method of Embodiment AO, wherein the optical change comprises a color change.

Embodiment AQ is the method of any one of Embodiments AE through AP, wherein detecting the microbial colony comprises optically detecting a gas bubble proximate the colony in the growth compartment.

Embodiment AR is the method of any one of Embodiments AN through AQ, wherein enumerating one or more microbial colonies further comprises distinguishing carbon dioxide-producing colonies from non-carbon dioxide-producing colonies.

Objects and advantages of this invention are further illustrated by the following examples, but the particular materials and amounts thereof recited in these examples, as well as other conditions and details, should not be construed to unduly limit this invention.

EXAMPLES

Example 1

Preparation of a Self-Contained Anaerobic Environment-Generating Culture Device

A self-contained anaerobic environment-generating culture device according to the culture device in FIG. 1 was constructed. The base consisted of 5 mil (0.127 mm) thickness polyester film (MELINEX Grade 377 biaxially-oriented polyester (PET) film, obtained from DuPont Teijin, Chester, Va.). A nutrient powder formulation (listed in Table 1) and guar gum (16 g/L) were stirred in deionized water to achieve a substantially uniform mixture. The pH of the mixture was targeted to be 5.8+/−0.5 and adjusted with acid or base if needed to meet the target value. The mixture was knife-coated onto the base as described in U.S. Pat. No. 4,565,783, and dried for 8 minutes at 210° F. (98.9° C.) in a convection oven. The nutrient layer was coated to a thickness that resulted in a target coating weight (after drying) of 0.56 g/24 $in^2$ (3.6 $mg/cm^2$). After drying, a polyethylene film spacer (Optimum Plastics, Bloomer, Wis.)

approximately 20 mil (0.508 mm) thick was adhered to the dried coating on the base via a thin layer of a pressure-sensitive adhesive (98 wt % isooctyl acrylate copolymerized with 2 wt % acrylic acid). The spacer contained a 2⅜-inch (6.03 cm) diameter circular opening that defined the hole in the spacer illustrated in FIG. 1. The circular opening defined the perimeter of the growth compartment of the device.

Sodium ascorbate (Sigma-Aldrich Corporation, St. Louis, Mo.) and sodium bicarbonate (Sigma-Aldrich Corporation) were individually milled and then passed through a 140 mesh sieve (resulting particle size less than 106 micron). A homogeneous mixture of guar gum (89.75 wt %, available from DuPont Danisco, Copenhagen, Denmark), sieved sodium ascorbate (10 wt %), and sieved sodium bicarbonate (0.25 wt %) was prepared. The coversheet consisted of clear polyester (PET) film (0.073 mm thick) that was coated on one side with a second pressure sensitive adhesive (96 wt % isooctyl acrylate copolymerized with 4% acrylamide) to a coat weight of 0.2 g/24 in$^2$ (1.3 mg/cm$^2$). The homogeneous mixture of guar gum, sieved sodium ascorbate, and sieved sodium bicarbonate was then powder coated onto the adhesive of the coversheet. The coversheet was attached to the base along one edge using a double-sided adhesive tape and the devices were cut into approximately 3" (7.6 cm) by 4" (10.1 cm) rectangles similar to those shown in FIG. 1. The coated side of the coversheet was oriented to face the spacer and growth compartment.

TABLE 1

Nutrient powder formulation used to coat base of the device of Example 1.

| Component | Amount (g/L) | Source |
|---|---|---|
| Enzymatic digest of casein | 10 | Alpha Biosciences, Baltimore, MD |
| Porcine peptone | 10 | Alpha Biosciences, Baltimore, MD |
| Yeast extract | 4 | Alpha Biosciences, Baltimore, MD |
| Ammonium citrate | 1 | Avantor, Center Valley, PA |
| Sodium acetate | 2.5 | EMD Millipore, Billerica, MA |
| Neutral red dye | 0.1 | Sigma-Aldrich Corp, St. Louis, MO |
| Magnesium sulfate heptahydrate | 0.2 | Avantor, Center Valley, PA |
| Manganese sulfate monohydrate | 0.05 | EMD Millipore, Billerica, MA |
| 2-(N-morpholino)ethanesulfonic acid | 23.45 | Avantor, Center Valley, PA |
| 2-(N-morpholino)ethanesulfonic acid sodium salt | 7.05 | Amresco, Solon, OH |
| Glucose | 20 | Hardy Diagnostics, Santa Maria, CA |
| Maltose | 20 | Amresco, Solon, OH |
| Polyoxyethylenesorbitan monooleate | 1.08 | Amresco, Solon, OH |
| Amphotericin B | 0.01 | Sigma-Aldrich Corp, St. Louis, MO |

Example 2

A self-contained anaerobic environment-generating culture device was prepared according to the description of Example 1 with the exception that instead of coating with the powder mixture of Example 1 the adhesive of the coversheet was coated with a powder mixture of guar gum (89.7 wt %), sodium ascorbate (10 wt %), and sodium bicarbonate (0.3 wt %).

Example 3

A self-contained anaerobic environment-generating culture device was prepared according to the description of Example 1 with the exception that instead of coating with the powder mixture of Example 1 the adhesive of the coversheet was coated with a powder mixture of guar gum (89.5 wt %), sodium ascorbate (10 wt %), and sodium bicarbonate (0.5 wt %).

Example 4

A self-contained anaerobic environment-generating culture device was prepared according to the description of Example 1 with the exception that instead of coating with the powder mixture of Example 1 the adhesive of the coversheet was coated with a powder mixture of guar gum (89.0 wt %), sodium ascorbate (10 wt %), and sodium bicarbonate (1.0 wt %).

Example 5

A self-contained anaerobic environment-generating culture device was prepared according to the description of Example 1 with the exception that instead of coating with the powder mixture of Example 1 the adhesive of the coversheet was coated with a powder mixture of guar gum (88.0 wt %), sodium ascorbate (10 wt %), and sodium bicarbonate (2.0 wt %).

Example 6

$CO_2$ Concentration Measurements in Devices of Examples 1-5

The self-contained anaerobic environment-generating culture devices of Examples 1-5 were monitored for $CO_2$ generation using a $pCO_2$ mini v2 fiber optic transmitter (PreSens Precision Sensing GmbH, Regensburg, DE cat #200001207) with vendor provided software for $CO_2$ tension measurement. Each device was opened by lifting the coversheet to expose the growth region of the growth compartment. One milliliter of sterile Butterfield's buffer was deposited into the growth compartment of each plate. A thin $CO_2$ sensor (5 mm in diameter and 200 microns thick) (Planar $pCO_2$ Minisensor Spot, PreSens Precision Sensing GmbH, cat #200001178) was immediately placed into the hydrated growth compartment and the coversheet was gently lowered until it contacted the hydrated growth region and the spacer. A flat, plastic spreader was pressed on the closed device to spread the liquid throughout the growth compartment. After closing the device, the fluorescence from the sensor was monitored using a polymer optical fiber cable to the transmitter. Measurements of $CO_2$ concentration in the hydrated growth compartment were recorded immediately after closing the device and 90 minutes later. In Table 2 the mean fold increase in $CO_2$ concentration measured after 90 minutes is reported (n=5).

TABLE 2

| Culture Device | Fold Increase in Measured $CO_2$ Concentration |
|---|---|
| Example 1 | 3.9 |
| Example 2 | 9.4 |
| Example 3 | 5.5 |

TABLE 2-continued

| Culture Device | Fold Increase in Measured $CO_2$ Concentration |
|---|---|
| Example 4 | 4.2 |
| Example 5 | 9.2 |

Example 7

Preparation and Use of a Self-Contained Anaerobic Environment-Generating Culture Device A self-contained anaerobic environment-generating culture device according to the culture device in FIG. 1 was constructed. The base was coated and prepared according to the procedure described in Example 1 with the only exception that guar gum (14 g/L) was combined with the nutrient formulation of Table 3 instead of the formulation in Table 1.

Sodium ascorbate (Sigma-Aldrich Corporation, St. Louis, Mo.) and sodium bicarbonate (Sigma-Aldrich Corporation) were individually milled and then passed through a 140 mesh sieve (resulting particle size less than 106 micron). A homogeneous mixture of guar gum (89.7 wt %, available from DuPont Danisco, Copenhagen, Denmark), sieved sodium ascorbate (10 wt %), and sieved sodium bicarbonate (0.3 wt %) was prepared. The coversheet consisted of clear polyester (PET) film (0.073 mm thick) that was coated on one side with a second pressure sensitive adhesive (96 wt % isooctyl acrylate copolymerized with 4% acrylamide) to a coat weight of 0.2 g/24 in$^2$ (1.3 mg/cm$^2$). A trace amount of triphenyl tetrazolium chloride (about 0.48 mg/24 in$^2$ (0.003 mg/cm$^2$)) was incorporated in the adhesive. The homogeneous mixture of guar gum, sieved sodium ascorbate, and sieved sodium bicarbonate was then powder coated onto the adhesive of the coversheet. The coversheet was attached to the base along one edge using a double-sided adhesive tape and the devices were cut into approximately 3" (7.6 cm) by 4" (10.1 cm) rectangles similar to those shown in FIG. 1. The coated side of the coversheet was oriented to face the spacer and growth compartment.

Individual samples of the bacterial strains *Lactobacillus* species, *Leuconostoc mesenteroides* ssp *mesenteroides*, *Leuconostoc mesenteroides* ssp *dextranicum*, *Lactobacillus brevis*, *Lactobacillus plantarum*, *Lactobacillus delbruekii*, *Streptococcus alactolyticus*, *Lactococcus garvieae*, and *Pediococcus acidilactici* were obtained as natural isolates from food and beverage samples. Individual suspensions were prepared in Butterfield's buffer and serially diluted to obtain final suspensions having concentrations (of individual organisms) that provided CFU counts of about 100. One milliliter of each suspension was used to inoculate individual culture devices made according to the Example. The culture devices were inoculated by lifting the coversheet to expose the growth region of the growth compartment, pipetting the one milliliter suspension into the growth compartment, gently lowering the coversheet until it contacted the suspension and the spacer, and gently pressing a flat plastic spreader onto the closed device to spread the liquid suspension throughout the growth compartment.

After inoculation the culture devices were incubated at 32° C. for 48 hours in an aerobic incubator. Following incubation, the red-colored colonies in each culture device were counted by visual examination. The mean colony count (n=2) was determined for each organism.

As a comparative reference, agar plates were also inoculated with individual suspensions of the same dilution and volume as used above with the culture device of this Example. The agar plate were prepared using *Lactobacilli* MRS Agar (Becton Dickinson Corporation, New Franklin, N.J.). The agar (70 g) was sequentially suspended in 1 L of purified water; boiled for 1 minute to dissolve the powder; autoclaved at 121° C. for 15 minutes; and cooled to 45-50° C. The cooled medium (15-20 mL per dish) was then poured into a sterile Petri dishes that contained 1 mL of the individual sample suspension. The inoculum was distributed throughout the medium by rotating the plate in one direction and then the opposite direction. The inoculated dish was then placed in an anaerobic chamber together with a gas-generating sachet (GASPAK EZ Anaerobe Sachet, Becton Dickinson Corp.) that provided an anaerobic atmosphere during the incubation period. The agar plates were incubated at 32° C. for 48 hours. Following incubation, the colonies on the plates were counted by visual examination. The mean colony count (n=2) was determined for each organism.

In Table 4, the ratio of the mean colony count determined using the culture device of the Example compared to the mean colony count determined using a reference agar plate is displayed for each organism tested [i.e. Ratio=(mean colony count using the culture device of the Example)/(mean colony count using the reference agar plate)].

TABLE 3

Nutrient powder formulation used to coat the base of the device of Example 7.

| Component | Amount (g/L) | Source |
|---|---|---|
| Enzymatic digest of casein | 10 | Alpha Biosciences, Baltimore, MD |
| Porcine peptone | 10 | Alpha Biosciences, Baltimore, MD |
| Yeast extract | 4 | Alpha Biosciences, Baltimore, MD |
| Ammonium citrate | 1 | Avantor, Center Valley, PA |
| Sodium acetate | 2.5 | EMD Millipore, Billerica, MA |
| Neutral red dye | 0.1 | Sigma-Aldrich Corp, St. Louis, MO |
| Crystal violet dye | 0.002 | Sigma-Aldrich Corp, St. Louis, MO |
| Magnesium sulfate heptahydrate | 0.2 | Avantor, Center Valley, PA |
| Manganese sulfate monohydrate | 0.05 | EMD Millipore, Billerica, MA |
| 2-(N-morpholino)ethanesulfonic acid | 18.45 | Avantor, Center Valley, PA |
| 2-(N-morpholino)ethanesulfonic acid sodium salt | 12.04 | Amresco, Solon, OH |
| Glucose | 20 | Hardy Diagnostics, Santa Maria, CA |
| Maltose | 20 | Amresco, Solon, OH |
| Polyoxyethylenesorbitan monooleate | 1.08 | Amresco, Solon, OH |
| Amphotericin B | 0.02 | Sigma-Aldrich Corp, St. Louis, MO |

Table 4 Colony Count Ratios for the Bacterial Strains of Example 7 [Ratio=(mean colony count using the culture device of Example 7)/(mean colony using the reference agar plate)]

TABLE 4

Colony Count Ratios for the Bacterial Strains of Example 7
[Ratio = (mean colony count using the culture device
of Example 7)/(mean colony using the reference agar plate)]

|  | Ratio |
| --- | --- |
| Lactobacillus species | 0.95 |
| Leuconostoc mesenteroides ssp mesenteroides | 1.04 |
| Leuconostoc mesenteroides ssp dextranicum | 0.88 |
| Lactobacillus brevis | 1.31 |
| Lactobacillus plantarum | 1.01 |
| Lactobacillus delbruekii | 1.11 |
| Streptococcus alactolyticus | 1.24 |
| Lactococcus garvieae | 0.85 |
| Pediococcus acidilactici | 0.99 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A culture device for enumerating colonies of a target microorganism, the device comprising:
   a base having opposing inner and outer surfaces;
   a coversheet having opposing inner and outer surfaces;
   a nonporous spacer member disposed between the base and the cover sheet, wherein the spacer member is coupled to the base or the coversheet, wherein the spacer member comprises an aperture that defines a shape and a depth of a growth compartment, wherein the spacer member and the growth compartment are disposed between the inner surface of the base and the inner surface of the coversheet;
   an effective amount of a dry oxygen-scavenging reagent disposed in the growth compartment;
   a dry, cold-water-soluble gelling agent disposed in the growth compartment, wherein the gelling agent is adhered to the base or the coversheet in the growth compartment;
   a dry buffer system disposed in the growth compartment such that, when the growth compartment is hydrated with a predetermined volume of deionized water, forms an aqueous mixture with a pH less than or equal to 6.35, wherein the dry buffer system comprises a component selected from the group consisting of 2-(N-morpholino)ethane sulfonic acid, succinic acid, and sodium succinate; and
   an effective amount of a dry carbon dioxide-generating reagent disposed in the growth compartment.

2. The culture device of claim 1, wherein the oxygen scavenging reagent consists essentially of particles having a diameter of less than 106 microns.

3. The culture device of claim 1, wherein the carbon dioxide-generating reagent consists essentially of particles having a diameter of less than 106 microns.

4. The culture device of claim 1, further comprising a dry nutrient disposed in the growth compartment, the nutrient selected to facilitate growth of the target microorganism.

5. The culture device of claim 1, further comprising a first indicator reagent disposed in the growth compartment, the first indicator reagent selected for detecting growth of the target microorganism.

6. The culture device of claim 1, further comprising an effective amount of a selective agent disposed in the growth compartment, the selective agent selected to inhibit growth of a non-target microorganism.

7. The culture device of claim 1, further comprising an effective amount of a reducing agent disposed in the growth compartment.

8. The culture device of claim 1, wherein the carbon dioxide-generating reagent comprises a metal carbonate.

9. The culture device of claim 1:
   wherein the inner surface of the base has a first adhesive adhered thereto;
   wherein one or more first component disposed in the growth compartment is adhered to the first adhesive;
   wherein the first component is selected from the group consisting of the gelling agent, the oxygen-scavenging reagent, the buffer system, a nutrient, an indicator reagent, a selective agent, a reducing agent, and a combination of any two or more of the foregoing first components.

10. The culture device of claim 1:
    wherein the inner surface of the coversheet has a second adhesive adhered thereto;
    wherein one or more third component disposed in the growth compartment is adhered to the second adhesive;
    wherein the third component is selected from the group consisting the gelling agent, the oxygen-scavenging reagent, the buffer system, a nutrient, an indicator reagent, a selective agent, a reducing agent, and a combination of any two or more of the foregoing third components.

11. The culture device of claim 1, wherein the carbon dioxide-generating reagent comprises a salt of carbonic acid.

12. The culture device of claim 1, wherein the oxygen-scavenging reagent comprises ferrous iron or a salt thereof or ascorbic acid or a salt thereof.

13. The culture device of claim 1, wherein the oxygen-scavenging reagent is disposed in the growth compartment in a quantity of about 1.5 micromoles/10 cm$^2$ surface area of the base or the coversheet in the growth compartment to about 15 micromoles/10 cm$^2$ surface area of the base or the coversheet in the growth compartment.

14. The culture device of claim 1, wherein the carbon dioxide-generating reagent is disposed in the growth compartment in a quantity of about 1 micromole/10 cm$^2$ surface area of the base or the coversheet in the growth compartment to about 15 micromoles/10 cm$^2$ surface area of the base or the coversheet in the growth compartment.

15. A method of detecting a microorganism in a sample, the method comprising:
    opening the culture device of claim 1 to provide access to the growth compartment therein;
    placing a predefined volume of aqueous liquid into the growth compartment;
    placing a sample into the growth compartment;
    closing the culture device;

wherein placing the aqueous liquid and the sample into the growth compartment and closing the culture device comprises forming a semi-solid microbial culture medium enclosed by the base, the coversheet, and the spacer of the culture device; the culture medium having a pH between 4.0 and 6.35;

incubating the culture device for a period of time sufficient to permit formation of a microbial colony in the culture medium; and detecting the microbial colony.

16. The method of claim 15, wherein placing the predetermined volume into the growth compartment comprises simultaneously placing the sample into the growth compartment.

17. The method of claim 15, wherein placing the predetermined volume into the growth compartment does not comprise simultaneously placing the sample into the growth compartment.

18. The method of claim 15, wherein placing the sample into the growth compartment comprises placing an additive into the growth compartment, wherein the additive comprises an effective amount of a selective agent or an indicator for detecting microbial growth.

19. The method of claim 15, wherein incubating the culture device for a period of time comprises incubating the culture device for the period of time in an aerobic atmosphere.

20. The method of claim 19, wherein detecting the microbial colony comprises optically detecting a gas bubble proximate the colony in the growth compartment.

* * * * *

UNITED STATES PATENT AND TRADEMARK OFFICE
CERTIFICATE OF CORRECTION

PATENT NO. : 10,995,356 B2
APPLICATION NO. : 15/569579
DATED : May 4, 2021
INVENTOR(S) : Bjork et al.

It is certified that error appears in the above-identified patent and that said Letters Patent is hereby corrected as shown below:

In the Specification

Column 5, Line 34, delete "Weisella." and insert -- Weissella --

Column 13, Line 6, delete "the the" and insert -- the --

Column 17, Line 25, delete "melaninogencia" and insert -- melaninogenica --

Column 24, Lines 10-11, delete "melaninogencia" and insert -- melaninogenica --

Column 27, Line 47, delete "delbruekii" and insert -- delbrueckii --

Column 29, Line 10 (Table 4), delete "delbruekii" and insert -- delbrueckii --

In the Claims

Column 29, Lines 65-66, delete "oxygen scavenging" and insert -- oxygen-scavenging --

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*